United States Patent
Reynolds et al.

(10) Patent No.: US 9,072,554 B2
(45) Date of Patent: Jul. 7, 2015

(54) ORTHOPEDIC IMPLANT

(75) Inventors: Joseph E. Reynolds, Cincinnati, OH (US); Alvin H. Crawford, Cincinnati, OH (US); Eric J. Wall, Cincinnati, OH (US)

(73) Assignees: Children's Hospital Medical Center, Cincinnati, OH (US); Spineform LLC, Cincinnati, OH (US)

( * ) Notice: Subject to any disclaimer, the term of this patent is extended or adjusted under 35 U.S.C. 154(b) by 1424 days.

(21) Appl. No.: 12/274,039

(22) Filed: Nov. 19, 2008

(65) Prior Publication Data

US 2009/0287249 A1    Nov. 19, 2009

Related U.S. Application Data

(63) Continuation-in-part of application No. 11/992,463, filed as application No. PCT/US2006/036884 on Sep. 21, 2006, now abandoned.

(60) Provisional application No. 60/719,076, filed on Sep. 21, 2005, provisional application No. 61/003,697, filed on Nov. 19, 2007.

(51) Int. Cl.
  *A61B 17/70* (2006.01)
  *A61B 17/064* (2006.01)
  *A61B 17/80* (2006.01)

(52) U.S. Cl.
  CPC ......... *A61B 17/8052* (2013.01); *A61B 17/0642* (2013.01); *A61B 17/7059* (2013.01); *A61B 17/8033* (2013.01); *A61B 17/8047* (2013.01); *A61B 17/8057* (2013.01); *A61B 17/809* (2013.01)

(58) Field of Classification Search
  CPC ............... A61B 17/80; A61B 17/8033; A61B 17/8047; A61B 17/8052; A61B 17/8057; A61B 17/809; A61B 17/0642
  USPC .......... 606/280–299, 309–318; 411/308–311, 411/415, 426
  See application file for complete search history.

(56) References Cited

U.S. PATENT DOCUMENTS

| | | |
|---|---|---|
| 82,181 A | 9/1868 | Tilestown |
| 431,175 A | 7/1890 | Southwick |
| 758,881 A | 5/1904 | Yost |
| 1,425,199 A | 8/1922 | Hartley |
| 1,638,477 A | 8/1927 | Dyer |
| 2,134,765 A | 11/1938 | Putnam |
| 2,398,603 A | 4/1946 | Soderberg |
| 2,919,621 A | 1/1960 | Langdon |

(Continued)

FOREIGN PATENT DOCUMENTS

| | | |
|---|---|---|
| EP | 0 026 970 A1 | 4/1981 |
| EP | 0 478 470 A1 | 1/1992 |

(Continued)

OTHER PUBLICATIONS

Beere Medical Precision Instruments, Bone Awls and Probes, Internet webpage, at least as early as Dec. 17, 2004, 2 pgs.

(Continued)

*Primary Examiner* — Michael T Schaper
(74) *Attorney, Agent, or Firm* — Faegre Baker Daniels LLP

(57) ABSTRACT

An orthopedic implant, illustratively a spinal staple, including pre-attached fasteners.

10 Claims, 10 Drawing Sheets

(56) References Cited

U.S. PATENT DOCUMENTS

| | | | |
|---|---|---|---|
| 3,693,616 A | 9/1972 | Roaf et al. | |
| 3,862,631 A | 1/1975 | Austin | |
| 4,041,939 A | 8/1977 | Hall | |
| 4,047,523 A | 9/1977 | Hall | |
| 4,047,524 A | 9/1977 | Hall | |
| 4,078,559 A | 3/1978 | Nissinen | |
| 4,401,112 A | 8/1983 | Rezaian | |
| 4,434,796 A | 3/1984 | Karapetian et al. | |
| 4,454,875 A | 6/1984 | Pratt et al. | |
| 4,462,395 A | 7/1984 | Johnson | |
| 4,570,618 A | 2/1986 | Wu | |
| 4,570,623 A | 2/1986 | Ellison et al. | |
| 4,573,454 A | 3/1986 | Hoffman | |
| 4,599,086 A | 7/1986 | Doty | |
| 4,651,724 A | 3/1987 | Berentey et al. | |
| 4,686,970 A | 8/1987 | Dove et al. | |
| 4,743,260 A | 5/1988 | Burton | |
| 4,776,851 A | 10/1988 | Bruchman et al. | |
| 4,793,335 A | 12/1988 | Frey et al. | |
| 4,841,960 A | 6/1989 | Garner | |
| 4,848,328 A | 7/1989 | Laboureau et al. | |
| 4,867,158 A | 9/1989 | Sugg | |
| 4,870,957 A | 10/1989 | Goble et al. | |
| 4,913,144 A | 4/1990 | Del Medico | |
| 4,955,910 A | 9/1990 | Bolesky | |
| 4,966,600 A | 10/1990 | Songer et al. | |
| 4,998,936 A | 3/1991 | Mehdian | |
| 5,002,574 A | 3/1991 | May et al. | |
| 5,011,484 A | 4/1991 | Breard | |
| 5,026,387 A | 6/1991 | Thomas | |
| 5,030,220 A | 7/1991 | Howland | |
| D320,081 S | 9/1991 | Johnson | |
| 5,053,038 A | 10/1991 | Sheehan | |
| 5,085,660 A | 2/1992 | Lin | |
| 5,092,866 A | 3/1992 | Breard et al. | |
| 5,092,868 A | 3/1992 | Mehdian | |
| 5,108,395 A | 4/1992 | Laurain et al. | |
| 5,116,340 A | 5/1992 | Songer et al. | |
| 5,147,361 A | 9/1992 | Ojima et al. | |
| 5,180,393 A | 1/1993 | Commarmond | |
| 5,199,146 A | 4/1993 | Grover et al. | |
| 5,213,569 A | 5/1993 | Davis | |
| D340,284 S | 10/1993 | Johnson | |
| 5,261,910 A | 11/1993 | Warden et al. | |
| 5,263,957 A | 11/1993 | Davison | |
| 5,306,301 A | 4/1994 | Graf et al. | |
| 5,318,566 A | 6/1994 | Miller | |
| 5,318,570 A | 6/1994 | Hood et al. | |
| 5,324,290 A | 6/1994 | Zdeblick et al. | |
| 5,330,481 A | 7/1994 | Hood et al. | |
| 5,342,380 A | 8/1994 | Hood | |
| 5,346,502 A | 9/1994 | Estabrook et al. | |
| 5,352,229 A | 10/1994 | Goble et al. | |
| 5,387,213 A | 2/1995 | Breard et al. | |
| 5,395,372 A | 3/1995 | Holt et al. | |
| 5,395,374 A | 3/1995 | Miller et al. | |
| 5,405,391 A | 4/1995 | Hednerson et al. | |
| 5,415,658 A | 5/1995 | Kilpela et al. | |
| 5,415,661 A | 5/1995 | Holmes | |
| 5,417,690 A | 5/1995 | Sennett et al. | |
| 5,423,820 A | 6/1995 | Miller et al. | |
| 5,425,767 A | 6/1995 | Steininger et al. | |
| 5,443,514 A | 8/1995 | Steffee | |
| 5,443,515 A | 8/1995 | Cohen et al. | |
| 5,449,359 A | 9/1995 | Groiso | |
| 5,456,722 A | 10/1995 | McLeod et al. | |
| D364,462 S | 11/1995 | Michelson | |
| 5,476,465 A | 12/1995 | Preissman | |
| 5,490,852 A | 2/1996 | Azer et al. | |
| 5,496,318 A | 3/1996 | Howland et al. | |
| 5,502,942 A | 4/1996 | Gras et al. | |
| 5,511,301 A * | 4/1996 | McGuire | 29/456 |
| 5,536,270 A | 7/1996 | Songer et al. | |
| 5,540,698 A | 7/1996 | Preissman | |
| 5,540,703 A | 7/1996 | Barker, Jr. et al. | |
| 5,545,168 A | 8/1996 | Burke | |
| 5,562,673 A | 10/1996 | Koblish et al. | |
| 5,569,253 A | 10/1996 | Farris et al. | |
| 5,569,264 A | 10/1996 | Tamminmaki et al. | |
| 5,570,982 A * | 11/1996 | Lautenschlager | 411/355 |
| 5,601,553 A * | 2/1997 | Trebing et al. | 606/86 B |
| 5,603,713 A | 2/1997 | Aust et al. | |
| 5,603,714 A | 2/1997 | Kaneda et al. | |
| D378,409 S | 3/1997 | Michelson | |
| 5,607,425 A | 3/1997 | Rogozinski | |
| 5,609,634 A | 3/1997 | Voydeville | |
| 5,620,443 A | 4/1997 | Gertzbein et al. | |
| 5,632,747 A | 5/1997 | Scarborough et al. | |
| 5,649,927 A | 7/1997 | Kilpela et al. | |
| 5,653,711 A | 8/1997 | Hayano et al. | |
| 5,662,654 A | 9/1997 | Thompson | |
| 5,662,655 A | 9/1997 | Laboureau et al. | |
| 5,669,917 A | 9/1997 | Sauer et al. | |
| 5,674,235 A | 10/1997 | Parisi | |
| 5,693,046 A | 12/1997 | Songer et al. | |
| 5,702,395 A | 12/1997 | Hopf | |
| 5,702,399 A | 12/1997 | Kilpela et al. | |
| 5,707,395 A | 1/1998 | Li | |
| 5,720,747 A | 2/1998 | Burke | |
| 5,720,748 A | 2/1998 | Kuslich et al. | |
| 5,720,751 A | 2/1998 | Jackson | |
| 5,722,977 A | 3/1998 | Wilhelmy | |
| 5,725,582 A | 3/1998 | Bevan et al. | |
| 5,741,260 A | 4/1998 | Songer et al. | |
| 5,782,919 A | 7/1998 | Zdeblick et al. | |
| 5,810,859 A | 9/1998 | DiMatteo et al. | |
| 5,855,581 A | 1/1999 | Koblish et al. | |
| 5,876,402 A | 3/1999 | Errico et al. | |
| 5,908,421 A | 6/1999 | Beger | |
| 5,993,458 A | 11/1999 | Vaitekunas et al. | |
| 5,993,477 A | 11/1999 | Vaitekunas et al. | |
| 6,004,326 A | 12/1999 | Castro et al. | |
| 6,017,345 A | 1/2000 | Richelsoph | |
| 6,027,523 A | 2/2000 | Schmieding | |
| 6,066,140 A | 5/2000 | Gertzbein et al. | |
| 6,113,602 A | 9/2000 | Sand | |
| 6,143,012 A | 11/2000 | Gausepohl | |
| 6,174,311 B1 | 1/2001 | Branch et al. | |
| 6,228,085 B1 | 5/2001 | Theken et al. | |
| 6,231,610 B1 | 5/2001 | Geisler | |
| 6,283,981 B1 | 9/2001 | Beaupre | |
| 6,296,643 B1 | 10/2001 | Hopf et al. | |
| 6,299,613 B1 | 10/2001 | Ogilvie et al. | |
| 6,309,393 B1 | 10/2001 | Tepic et al. | |
| 6,315,779 B1 | 11/2001 | Morrison et al. | |
| 6,325,805 B1 | 12/2001 | Ogilvie et al. | |
| 6,336,928 B1 | 1/2002 | Guerin et al. | |
| 6,413,259 B1 | 7/2002 | Lyons et al. | |
| 6,416,515 B1 | 7/2002 | Wagner | |
| 6,436,099 B1 | 8/2002 | Drewry et al. | |
| 6,481,760 B1 * | 11/2002 | Noel et al. | 285/334 |
| 6,497,715 B2 | 12/2002 | Satou | |
| 6,514,267 B2 | 2/2003 | Jewett | |
| 6,524,312 B2 | 2/2003 | Landry et al. | |
| 6,551,320 B2 | 4/2003 | Lieberman | |
| 6,565,574 B2 | 5/2003 | Michelson | |
| 6,592,587 B1 * | 7/2003 | Roger | 606/318 |
| 6,595,992 B1 | 7/2003 | Wagner et al. | |
| 6,602,255 B1 | 8/2003 | Campbell et al. | |
| 6,616,669 B2 | 9/2003 | Ogilvie et al. | |
| 6,623,484 B2 | 9/2003 | Betz et al. | |
| 6,626,926 B2 | 9/2003 | Friedman et al. | |
| 6,629,976 B1 | 10/2003 | Gnos et al. | |
| 6,682,534 B2 | 1/2004 | Patel et al. | |
| 6,746,450 B1 * | 6/2004 | Wall et al. | 606/280 |
| 7,087,057 B2 | 8/2006 | Konieczynski et al. | |
| 7,137,987 B2 | 11/2006 | Patterson et al. | |
| 7,163,561 B2 | 1/2007 | Michelson | |
| 7,175,624 B2 | 2/2007 | Konieczynski et al. | |
| 7,186,255 B2 | 3/2007 | Baynham et al. | |
| 7,285,121 B2 | 10/2007 | Braun et al. | |
| 7,374,557 B2 | 5/2008 | Conlon et al. | |
| 7,481,830 B2 | 1/2009 | Wall et al. | |
| 2002/0103497 A1 | 8/2002 | Satou | |

(56) References Cited

U.S. PATENT DOCUMENTS

| | | | |
|---|---|---|---|
| 2003/0204199 | A1 | 10/2003 | Novak et al. |
| 2004/0127899 | A1 | 7/2004 | Konieczynski et al. |
| 2004/0143270 | A1 | 7/2004 | Zucherman et al. |
| 2004/0172044 | A1 | 9/2004 | Grimm et al. |
| 2004/0177847 | A1 | 9/2004 | Foley et al. |
| 2004/0220569 | A1 | 11/2004 | Wall et al. |
| 2004/0220581 | A1 | 11/2004 | Foley et al. |
| 2004/0249388 | A1 | 12/2004 | Michelson |
| 2005/0113842 | A1 | 5/2005 | Bertagnoli et al. |
| 2005/0238459 | A1* | 10/2005 | Levey et al. .............. 411/308 |
| 2005/0277933 | A1 | 12/2005 | Wall et al. |
| 2006/0079961 | A1 | 4/2006 | Michelson |
| 2006/0149265 | A1* | 7/2006 | James et al. .............. 606/73 |
| 2007/0073297 | A1 | 3/2007 | Reynolds |
| 2007/0093826 | A1 | 4/2007 | Hawkes et al. |
| 2007/0123883 | A1 | 5/2007 | Ellis et al. |
| 2008/0045957 | A1 | 2/2008 | Landry et al. |
| 2008/0288000 | A1* | 11/2008 | Cawley .............. 606/291 |
| 2010/0100138 | A1 | 4/2010 | Reynolds et al. |

FOREIGN PATENT DOCUMENTS

| | | |
|---|---|---|
| EP | 0 545 830 A1 | 6/1993 |
| EP | 0 552 109 A1 | 7/1993 |
| EP | 0 625 336 A2 | 11/1994 |
| FR | 2 709 410 | 3/1995 |
| JP | 63-95060 | 4/1988 |
| JP | 3-75717 U | 7/1991 |
| JP | 7-79998 | 3/1995 |
| JP | 7-163580 | 6/1995 |
| JP | 8-507458 | 8/1996 |
| JP | 8-229052 | 9/1996 |
| JP | 10-277070 | 10/1998 |
| JP | 11-056870 | 2/1999 |
| WO | WO 91/16018 | 10/1991 |
| WO | WO 94/01057 | 1/1994 |
| WO | WO 94/26192 | 11/1994 |
| WO | WO 98/17189 | 4/1998 |
| WO | WO 98/48718 | 11/1998 |
| WO | WO 98/51226 | 11/1998 |
| WO | WO 99/56653 A1 | 11/1999 |
| WO | WO 2006/089145 A1 | 8/2006 |
| WO | WO 2006/138500 A2 | 12/2006 |
| WO | WO 2007/035892 A1 | 3/2007 |

OTHER PUBLICATIONS

Kmedic® Spinal Sourcebook, covers and pp. 33-34, 1999, 5 pgs.

Wall et al., "Endoscopic Discectomy Increases Thoracic Spine Flexibility as Effectively as Open Discectomy: A Mechanical Study in a Porcine Model," Spine, vol. 23(1), pp. 9-15, Jan. 1, 1998, 12 pgs.

Lonstein et al., "The Prediction of Curve Progression in Untreated Idiopathic Scoliosis During Growth," The Journal of Bone and Joint Surgery, vol. 66-A, No. 7, Sep. 1984, pp. 1061-1071.

A.D. Smith et al., "An Operation for Stapling Vertebral Bodies in Congenital Scoliosis," The Journal of Bone and Joint Surgery, vol. 36-A, No. 2, pp. 342-348, Apr. 1954.

D. I. Bylski-Austrow et al., Paper: "Endoscopic Nonfusion Spinal Hemiepiphysiodesis: Preliminary studies in a porcine model," Jan. 1999, 3 pgs.

Blount, MD, "A Mature Look at Epiphyseal Stapling," Clinical Orthopaedics and Related Research, No. 77, Jun. 1971, pp. 158-163.

Wojcik, MD et al., "An Analysis of the Effect of the Zielke Operation on S-shaped Curves in Idiopathic Scoliosis: A Follow-up Study Revealing Some Skeletal and Soft Tissue Factors Involved in Curve Progression," Spine, vol. 15, No. 8, 1990, 6 pgs.

McCarroll, MD et al., "Attempted Treatment of Scoliosis by Unilateral Vertebral Epiphyseal Arrest," The Journal of Bone and Joint Surgery, vol. 42-A, No. 6, Sep. 1960, 14 pgs.

Hopf et al., "CDH: preliminary report on a new anterior spinal instrumentation," European Spine Journal, Spring 1994, 6 pgs.

Ogon, MD et al., "Comparison Between Single-Screw and Triangulated, Double-Screw Fixation in Anterior Spine Surgery: A Biomechanical Test," Spine, vol. 21, No. 23, 1996, 7 pgs.

Blount, et al., "Control of Bone Growth by Epiphyseal Stapling: A Preliminary Report," The Journal of Bone and Joint Surgery, vol. 31-A, No. 3, Jul. 1949, 15 pgs.

Winter, "Convex Anterior and Posterior Hemiarthrodesis and Hemiepiphysiodesis in Young Children with Progressive Congenital Scoliosis ," Journal of Pediatric Orthopaedics, vol. 1, No. 4, 1981, 6 pgs.

Winter, "Convex Growth Arrest for Progressive Congenital Scoliosis Due to Hemivertebrae," Journal of Pediatric Orthopaedics, vol. 8, No. 6, 1988, 6 pgs.

Andrew et al., "Growth Arrest for Progressive Scoliosis: Combined Anterior and Posterior Fusion of the Convexity," The Journal of Bone and Joint Surgery, vol. 67-B, No. 2, Mar. 1985, 5 pgs.

Piggot, Frcs, "Growth Modification in the Treatment of Scoliosis," Orthopedics, vol. 10, No. 6, Jun. 1987, 8 pgs.

Goff, MD, "Histologic Arrangements from Biopsies of Epiphyseal Plates of Children Before and After Stapling," American Journal of Orthopedics, May, 1967, 3 pgs.

Stokes, PhD. et al., "Mechanical Modulation of Vertebral Body Growth; Implications for Scoliosis Progression," Spine, vol. 21, No. 10, 1996, 6 pgs.

Hopf et al., "Operative Treatment of Scoliosis With Cotrel-Dubousset-Hopf Instrumentation: New Anterior Spinal Device," Spine, vol. 22, No. 6, 1997, 11 pgs.

Mente, Ph.D. et al., "Progression of Vertebral Wedging in an Asymmetrically Loaded Rat Tail Model," Spine, vol. 22, No. 12, 1997, 5 pgs.

Haas, MD, "Retardation of Bone Growth by a Wire Loop," The Journal of Bone and Joint Surgery, vol. 27, No. 1, Jan., 1945, 12 pgs.

Nachlas, MD et al., "The Cure of Experimental Scoliosis by Directed Growth Control," The Journal of Bone and Joint Surgery, vol. 33-A, No. 1, 1951, 11 pgs.

Hall-Craggs et al., "The Effect of Epiphysial Stapling on Growth in Length of the Rabbit's Tibia and Femur," The Journal of Bone and Joint Surgery, vol. 51, No. 2, May 1969, 7 pgs.

Hall-Craggs et al., "Influence of Epiphyses on the Regulation of Bone Growth," Nature, vol. 221, Mar. 29, 1969, 1 pg.

Pazzaglia et al., "The Effects of Mechanical Forces on Bones and Joints: Experimental Study on the Rat Tail," The Journal of Bone and Joint Surgery, vol. 79-B, No. 6, Nov. 1997, 7 pgs.

Roaf, "The Treatment of Progressive Scoliosis by Unilateral Growth-Arrest," The Journal of Bone and Joint Surgery, vol. 45-B, No. 4, Nov. 1963, 15 pgs.

King, et al., "Transpedicular Convex Anterior Hemiepiphysiodesis and Posterior Arthrodesis for Progressive Congenital Scoliosis," Spine, vol. 17, No. 8S, 1992, 4 pgs.

Roaf, "Vertebral Growth and Its Mechanical Control," The Journal of Bone and Joint Surgery, vol. 42-B, No. 1, Feb. 1960, 20 pgs.

International Preliminary Report on Patentability from the International Searching Authority in priority application No. PCT/US2006/036884, dated Apr. 3, 2008, 5 pgs.

* cited by examiner

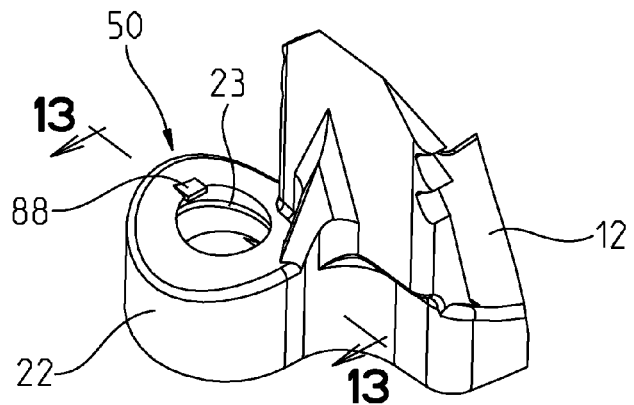
FIG. 12
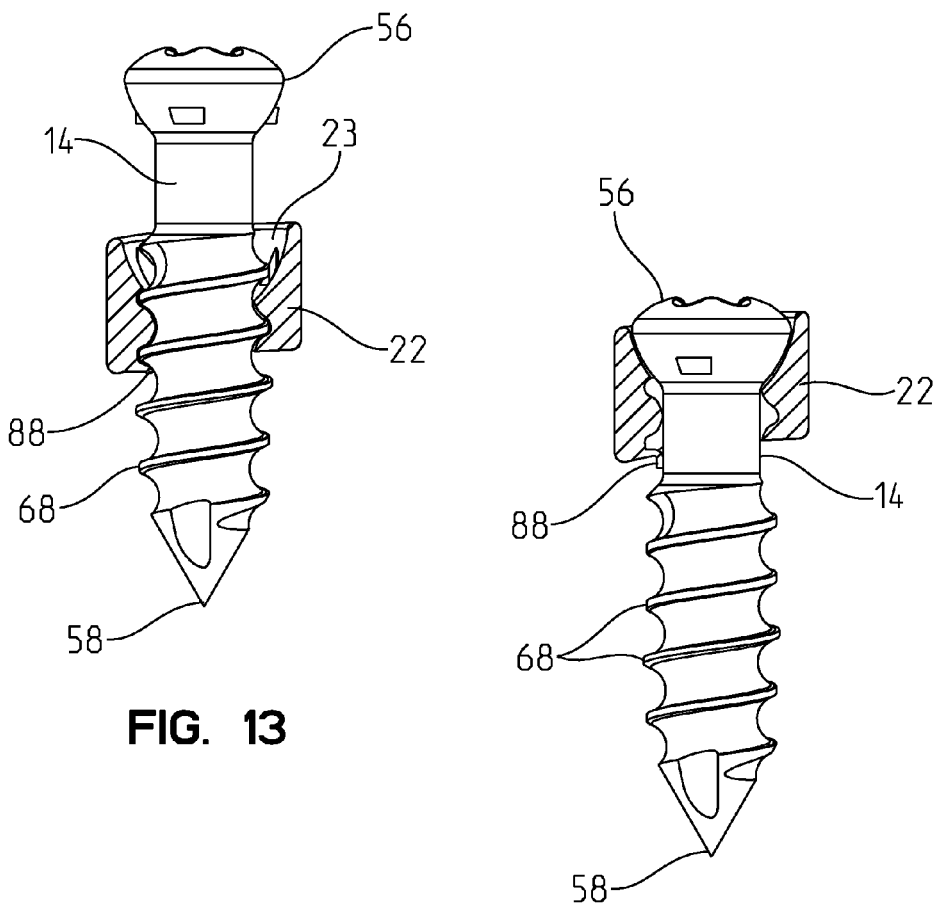
FIG. 13
FIG. 14

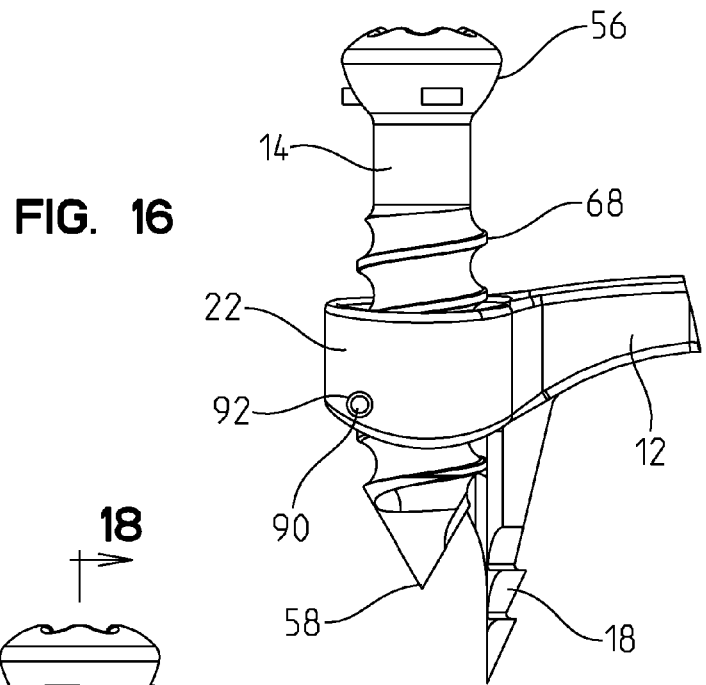
FIG. 16
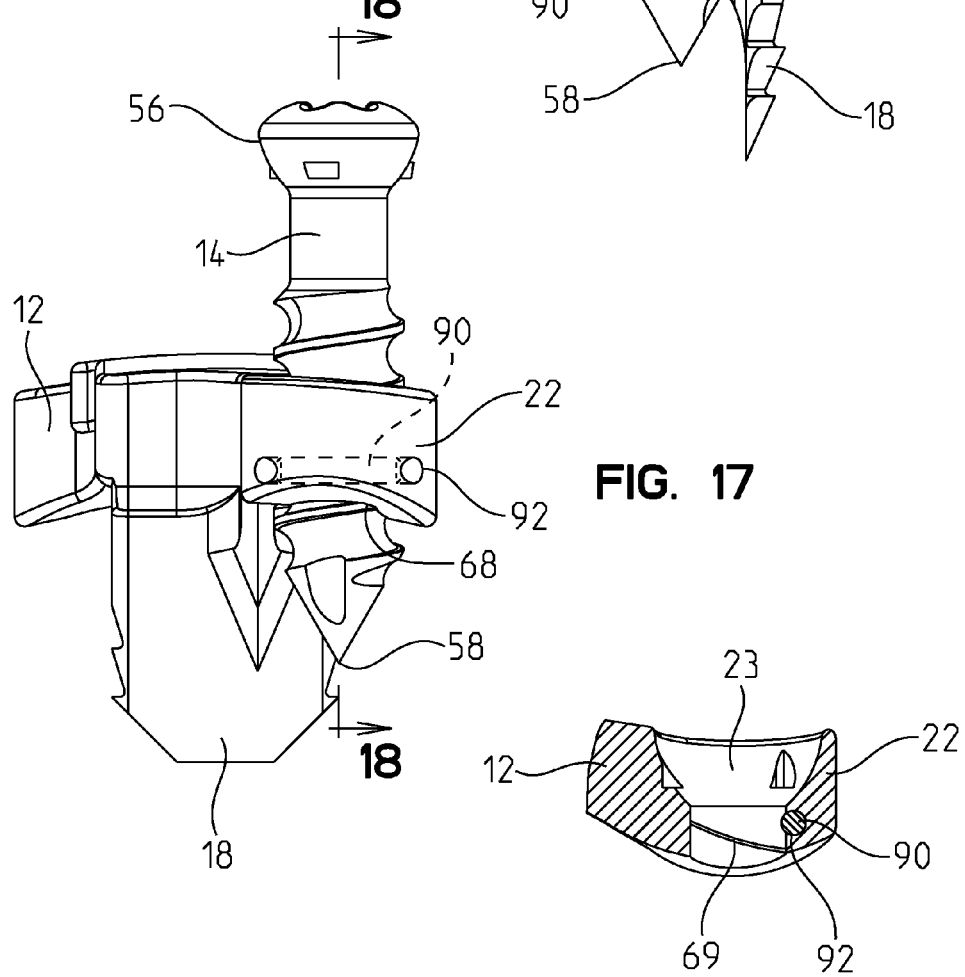
FIG. 17
FIG. 18

ORTHOPEDIC IMPLANT

CROSS-REFERENCE TO RELATED APPLICATIONS

The present application is a continuation-in-part of U.S. patent application Ser. No. 11/992,463, filed Mar. 21, 2008, which is the national phase under 35 U.S.C. §371 of PCT International Application No. PCT/US2006/036884, filed Sep. 21, 2006, which claims the benefit of U.S. Provisional Patent Application Ser. No. 60/719,076, filed Sep. 21, 2005, and the present application further claims the benefit of U.S. Provisional Patent Application Ser. No. 61/003,697, filed Nov. 19, 2007, the disclosures of which are all hereby incorporated by reference herein.

BACKGROUND AND SUMMARY OF THE INVENTION

The present invention relates to orthopedic implants using pre-attached fasteners.

Placement of orthopedic implants often consists of fixing an implant member to bone using one or more fasteners (often comprising bone screws). Typically, this is done by holding the implant in place while retrieving fasteners from a kit and placing them one at a time through holes or slots in the implant. Alternatives exist where fasteners are inserted into bone first, then the implant attached to the fasteners.

However, minimally invasive orthopedic procedures often result in difficult fastener placement, especially while trying to align the implant. Space for fasteners, implant and instrumentation is at a premium, often resulting in difficulty maneuvering within confined spaces or near delicate anatomy. Fasteners may also be dropped, and require time for proper placement. Additionally, passing instruments into and out of minimally invasive surgical ports may result in procedure delays.

Therefore techniques and designs are needed that can reduce procedure steps, required maneuvering in restricted space, and/or instrument exchanges.

The illustrative embodiments of this disclosure relate to instruments and methods for installation of orthopedic implant devices in general and, more specifically, to devices used in the correction, arresting or slowing of abnormal curvature of the spine, including scoliosis, hyperlordosis and hypokyphosis.

It is anticipated that the embodiments of this disclosure will be equally useful for any orthopedic implant requiring fixation to bone by a fastener, including, but not limited to, bone plates, cervical plates, and thoracolumbar plates.

In an illustrative embodiment of the present disclosure, an orthopedic implant device includes a body having a first surface, a second surface opposed to the first surface and configured to face a bone, and a fastener receiving opening extending between the first and second surfaces. A bone screw is received within the fastener receiving opening of the body and is configured to be inserted into the bone. The bone screw extends between proximal and distal ends and includes a threaded portion. A releasable securing member is configured to pre-attach the bone screw to the body prior to placement of the bone screw within the bone in a secured mode of operation by resisting axial movement of the bone screw relative to the fastener receiving opening of the body.

According to a further illustrative embodiment of the present disclosure, an orthopedic implant device includes a spinal staple having a bridge member with an upper surface, an opposed lower surface, a first end, an opposed second end, a first leg proximate the first end and configured to be inserted into a first vertebra, and a second leg proximate the second end and configured to be inserted into a second vertebra. At least one fastener is configured to couple the spinal staple to at least one of the first vertebra and the second vertebra. A releasable securing member is configured to pre-attach the at least one fastener to the spinal staple prior to coupling of the spinal staple to the first vertebra and the second vertebra.

According to another illustrative embodiment of the present disclosure, a pre-assembled implant device includes an orthopedic implant, and a bone screw pre-attached to the implant prior to placement within a bone.

According to yet another illustrative embodiment of the present disclosure, a method of inserting an orthopedic implant device includes the steps of providing an implant body including a receiving opening, inserting a bone screw into the receiving opening of the implant body, and securing the bone screw to the implant body to resist axial movement of the bone screw relative to the receiving opening. The method further includes the steps of applying a predetermined force to the bone screw in order to release the bone screw for axial movement relative to the implant, and inserting the bone screw into bone.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 12 is a partial isometric view of a further illustrative orthopedic implant device for use with pre-attached fasteners;

FIG. 13 is a cross-sectional view taken along line 13-13 of FIG. 12 showing the bone screw in a secured mode;

FIG. 14 is a cross-sectional view similar to FIG. 13 showing the bone screw in a locked (down) position;

FIG. 16 is a partial side elevation view of the implant body and pre-attached fasteners of FIG. 15;

FIG. 17 is an end view of the implant of FIG. 15;

FIG. 18 is a cross-sectional view taken along line 18-18 of FIG. 17;

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

It has been found that by attaching fasteners, and more specifically bone screws, to an orthopedic implant body prior to placement of either in the patient, several instrument exchanges can be avoided. Since the screws are pre-aligned, this step and the associated maneuvering step may be eliminated.

The illustrative embodiment implant device allows the fasteners (illustratively bone screws) to be pre-assembled in the implant body to eliminate the added steps of placing the fasteners as a part of the surgical procedure. The screws may also be utilized to hold or attach the implant body to the insertion instrument and to allow for easy disengagement (or detachment) following placement.

Pre-assembly is enhanced by the inclusion of at least one feature to prevent the fastener from moving out of position. This feature may hold the fastener in a specific position or within a position range. Possible features illustratively include mating threads providing an interference fit, retaining clips, spring clips or resistive materials, such as adhesives. These features may be a part of the fastener, implant body, insertion instrument, or combinations thereof. In one illustrative embodiment, an interference thread on the fastener creates frictional resistance with the mating thread of the implant body, preventing axial movement during initial placement of the implant, but allowing the screw to be advanced into bone thereafter. This interference thread may include a screw thread which is oversized for a single revolution relative to the internal thread of the implant body.

Illustratively, the fasteners are configured to pierce cortical bone. This may be accomplished with a self drilling fastener or with a fastener which acts as an awl during positioning of the implant body. In the illustrative embodiment, the tips of the pre-attached screws extend from the implant body far enough to act as an awl and pierce the cortical bone during positioning of the implant device. Furthermore, this screw portion extending beyond the implant body illustratively contains a segment that is unthreaded and has a smaller diameter than the minor diameter of the screw to facilitate bone penetration. The tip has an acute angle and may be either sharp or dull.

Figure 1:
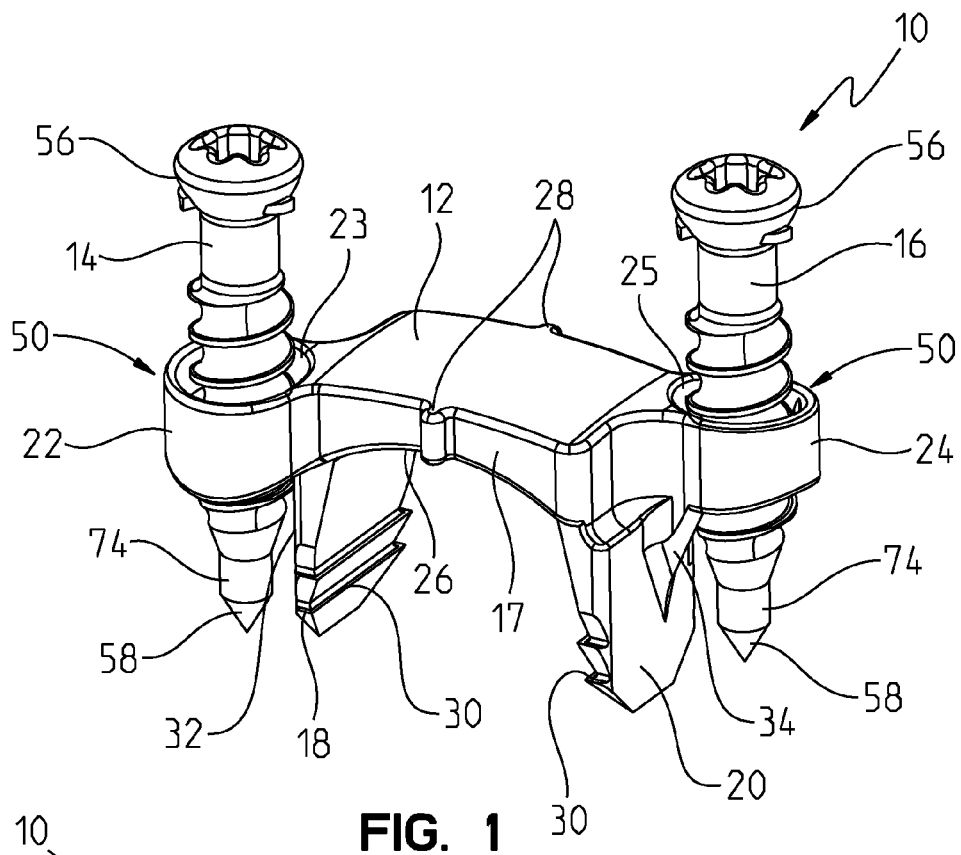
FIG. 1 is an isometric view of an orthopedic implant device including pre-attached fasteners.

FIG. 1 is an isometric view of an illustrative embodiment pre-assembled orthopedic implant device 10 including a body 12, illustratively a spinal staple, and pre-attached fasteners 14 and 16, illustratively bone screws, prior to insertion into a patient. While the illustrative implant device 10 is a spinal correction implant, the implant device 10 could be a cervical plate or any orthopedic implant that requires the use or placement of fasteners 14 and 16. In one illustrative embodiment, the implant device 10 includes a bridge member 17 connecting a pair of spaced apart legs 18 and 20. The staple legs 18 and 20 are configured to be driven through cortical bone to provide additional bone fixation. Extending outwardly from the bridge member 17 proximate the legs 18 and 20, are a left fastener retaining portion 22 including a fastener receiving opening 23, and a right fastener retaining portion 24 including a fastener receiving opening 25. The body 12 is illustratively formed of a biocompatible material, such as titanium or a titanium alloy. Although reference may be made throughout this description to terms implying direction, such as left, right, front, back, upper and lower, unless otherwise noted, these terms are used for convenience and should not be read as limiting the implant device 10 to any particular orientation.

The bridge member 17 couples the left fastener retaining portion 22 to the right fastener retaining portion 24. The lower surface 26 of the bridge member 17 is illustratively concave in a direction from a left end to a right end, and from a front side to a back side. In the illustrative embodiment, arcuate protrusions define centering portions 28 extending laterally outwardly from the bridge member 17 and are configured to cooperate with an insertion tool.

Left and right legs 18 and 20 extend downwardly from the lower surface 26 of the left and right ends of the bridge member 17. Barbs 30 illustratively project outwardly from the legs 18 and 20 toward a center of the bridge member 17. Anti-rotation or stabilization members or plates 32 and 34 may illustratively be located outboard of, and perpendicular to, each leg 18 and 20. More particularly, a left anti-rotation member 32 extends between the left fastening retaining portion 22 of the left leg 18, and a right anti-rotation member 34 extends between the right fastener retaining portion 24 and the right leg 20. The anti-rotation member members 32 and 34 are configured to reduce relative motion between adjacent vertebrae 40, while also preventing relative rotation of the fastener retaining portions 22 and 24.

Figure 21:
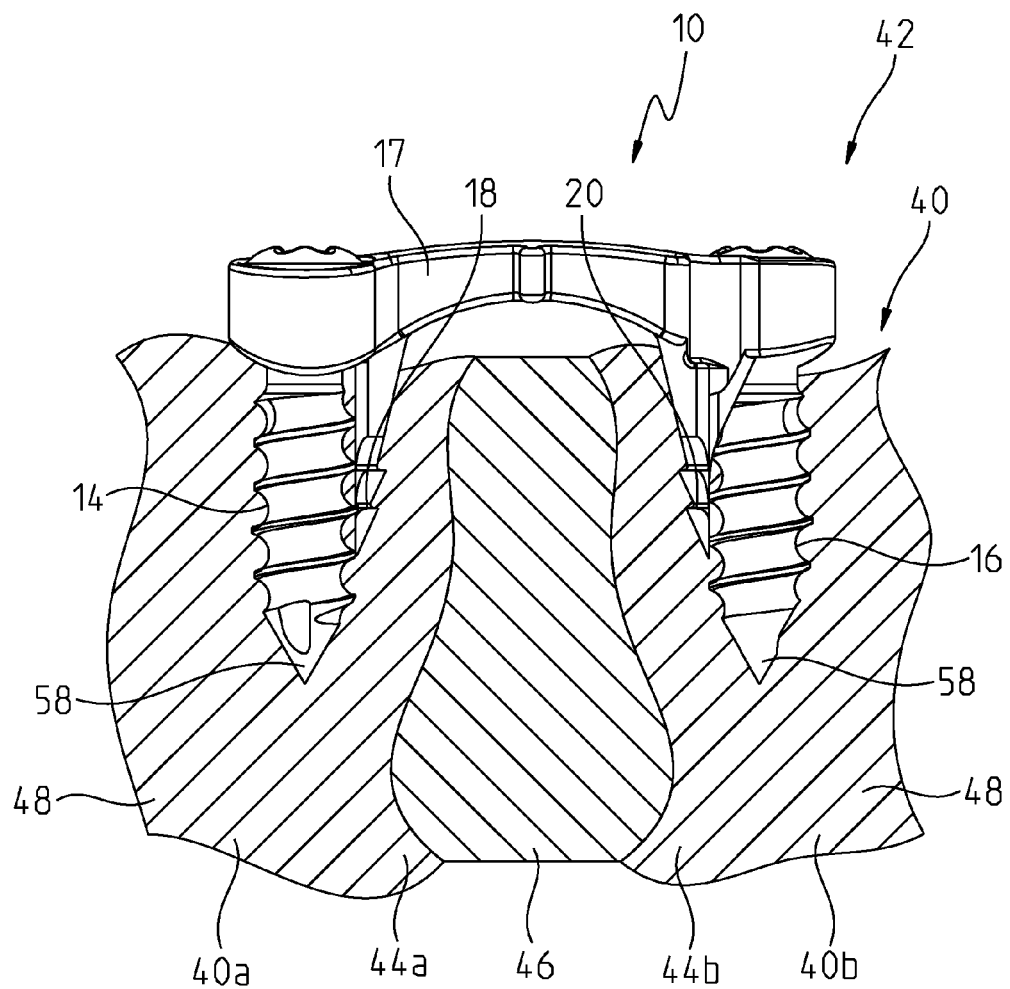
FIG. 21 is a cross-sectional view of the implant body and fasteners in a spine following placement and tightening of the fasteners.

A plurality of spinal implant devices 10 may be inserted into the vertebrae 40 of a person having an immature or growing spine 42 exhibiting scoliosis or other spinal deformity. The legs 18 and 20 are configured such that the implant device 10 will bridge longitudinally or lengthwise aligned, adjoining vertebrae 40a and 40b having confronting endplate growth centers 44a and 44b, and an intervening disc 46 therebetween (FIG. 21). The implant devices 10 are illustratively driven into the bone 48 of adjoining vertebrae 40a and 40b on the convex side of the curved spine 42.

Bone screws 14 and 16 are illustratively inserted into the vertebrae 40a and 40b to further secure the fastener retaining portions 22 and 24 to the spine 42. The bone screws 14 and 16 are illustratively formed of a biocompatible material such as titanium or a titanium alloy. Additional features of the spinal implant device 10 are further detailed in U.S. patent application Ser. No. 11/126,782, filed May 11, 2005, the disclosure of which is expressly incorporated by reference herein.

Figure 2:
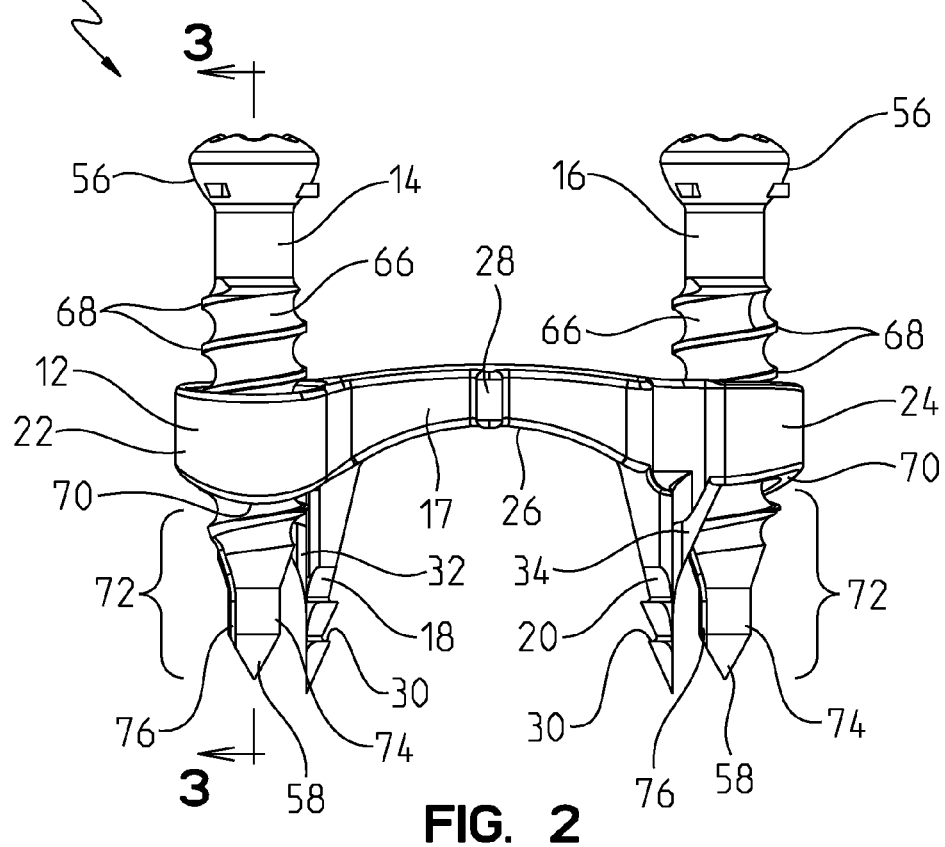
FIG. 2 is a side elevation view of the implant body and fasteners of FIG. 1.
Figure 3:
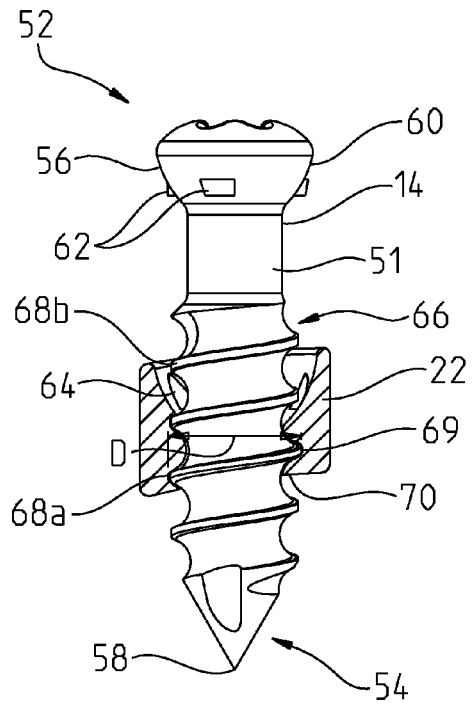
FIG. 3 is a cross-sectional view of the implant body taken along line 3-3 of FIG. 2, showing the fastener in a secured mode.
Figure 4:
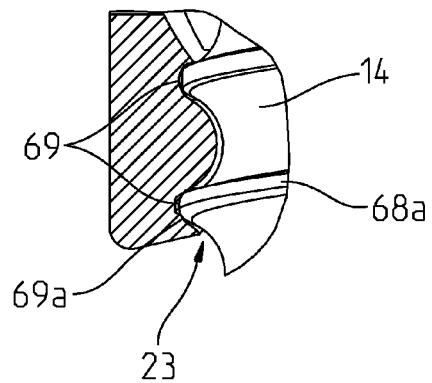
FIG. 4 is a detailed view of FIG. 3.

FIG. 2 is a side view of the illustrative embodiment pre-assembled implant device 10 including a body or staple 12 and pre-attached screws 14 and 16. The screws 14 and 16 are pre-assembled or pre-attached to the staple 12, illustratively through a releasable securing member 50 that prevents the screws 14 and 16 from moving relative to the staple 12. As further detailed herein, the screws 14 and 16 may be pre-attached or coupled to the staple 12 via a variety of means, including, but not limited to, mating threads (external screw threads and internal staple threads), retaining clips, spring clips, or resistive material, such as adhesives. Each embodiment of releasable securing member 50 is illustratively configured to pre-attach the respective bone screw 14, 16 to the staple 12 prior to placement of the bone screw 14, 16 in bone 48 in a secured mode of operation by resisting axial movement of the bone screw 14, 16 relative to the fastener receiving opening 23, 25 of the staple 12. More particularly, the releasable securing member 50 is illustratively configured to resist rotational movement and resulting axial movement of the bone screw 14, 16 in the secured mode of operation, and to permit rotational movement and resulting axial movement of the bone screw 14, 16 within the receiving opening 23, 25 in a released mode of operation.

With reference to FIGS. 3-6, an illustrative bone screw 14 includes an elongated shank 51 extending between proximal and distal ends 52 and 54. While bone screw 14 is further detailed below, it should be noted that bone screw 16 is substantially identical and, as such, the description applies equally to both bone screws 14 and 16. A head 56 is supported at the proximal end 52 and a bone engaging tip 58 is supported at the distal end 54. The head 56 may include a spherical surface 60 from which extend one or more protrusions 62. Each protrusion 62 is configured to engage with a recess 64 formed within the fastener receiving opening 23 of the implant device 10 to facilitate locking therebetween when the bone screw 14 has engaged the bone 48 and is in a lowered position within the staple 12. More particularly, cooperation between the protrusions 62 and recesses 64 prevent the bone screw 14 from reversing direction, thereby assuring that the bone screw 14 does not back out during normal motion of the spine 42 and other anatomical features after the bone screw 14 has been firmly secured within the bone 48. Additional details regarding this integral fastener retention mechanism is provided in U.S. patent application Ser. No. 11/227,820, filed Sep. 15, 2005, the disclosure of which is incorporated by reference herein.

A threaded portion 66 including a plurality of external threads 68 is supported by the shank 51 of each bone screw 14, 16 intermediate the respective proximal and distal ends 52 and 54. The external threads 68 are configured to cooperate with internal threads 69 formed within the receiving openings 23, 25. As further detailed herein, in the secured mode the tip 58 of each bone screw 14, 16 illustratively extends beyond the lower surface 70 of the respective retaining portion 22, 24.

In the illustrative embodiment of FIGS. 3-7, the releasable securing member 50 comprises an interference between at least one of the external screw threads 68 and at least one of the internal staple threads 69. Each bone screw 14, 16 may include such an interference by a single revolution of the external screw thread 68a being oversized relative to the internal staple thread 69a, thereby preventing axial movement of the screw 14, 16 relative to the staple 12 during initial placement within the patient, but allowing the respective screw 14, 16 to be rotationally moved and advanced thereafter.

In the secured mode of operation (FIGS. 3 and 4), at least one thread 68a of the bone screw 14, 16 interferes with at least one thread 69a of the bone receiving opening 23, 25. In one illustrative embodiment, the at least one external thread 68a of the bone screw 14, 16 has a major diameter (D) of about 4.2 mm, while the remaining threads 68b of the bone screw 14, 16 have a major diameter (d) of about 4.0 mm. In turn, the internal threads 69 of the corresponding fastener receiving opening 23, 25 have a major diameter of about 4.0 mm to threadably engage the external threads 68b of the bone screw 14, 16. As such, the oversized thread 68a of the bone screw 14, 16 interferes with the internal threads 69 of the receiving opening 23, 25, radially by about 0.1 mm (i.e., interference diameter of about 0.2 mm). Illustratively, the bone screw 14, 16 has a pitch of approximately 1.75 mm and a minor diameter of approximately 3 mm.

Since the interference between the threads 68a and 69a is relatively small (approximately less than 0.1 mm per side), the oversized external thread 68a is plastically or elastically deformed as it passes through the internal thread 68a without permanently damaging the threads 68 and 69. Moreover, the screw 14, 16 may be successively reversed and removed without causing damage to the threads 68 and 69.

Figure 5:
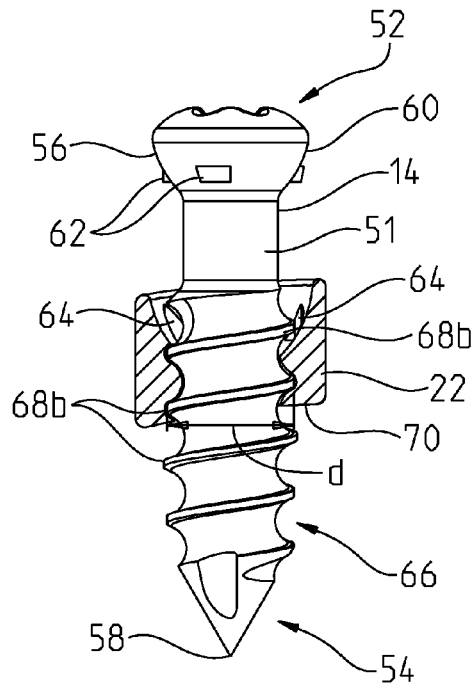
FIG. 5 is a cross-sectional view similar to FIG. 3, showing the fastener in a released mode.
Figure 6:
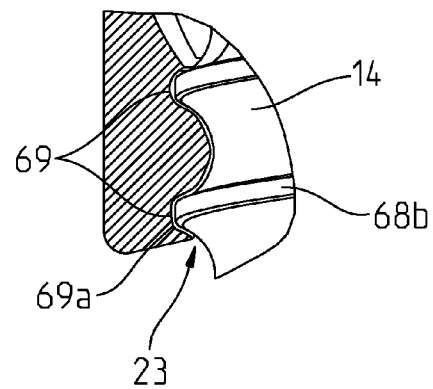
FIG. 6 is a detailed view of FIG. 5.
Figure 7:
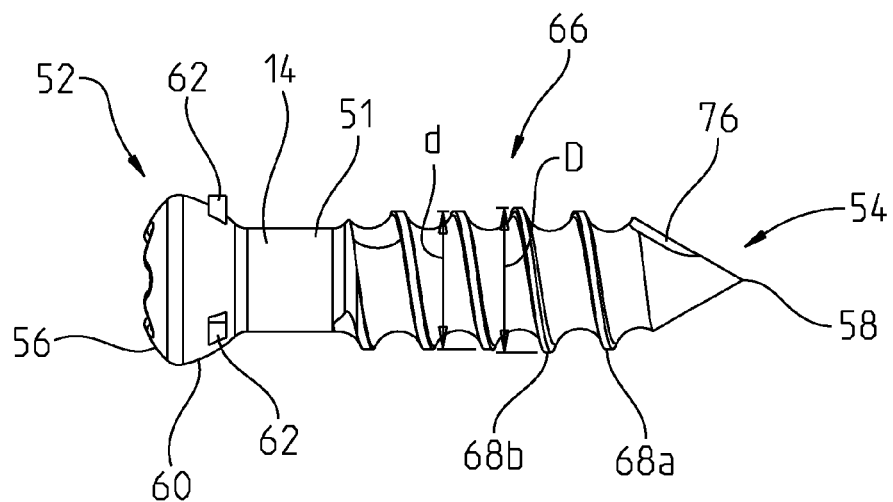
FIG. 7 is a side elevation view of an illustrative bone screw of FIG. 1.

While interference between the threads 68 and 69 of the bone screw 14, 16 and the respective fastener receiving opening 23, 25 provides a secured mode of operation, the coupling may be released by exerting a force on the bone screw 14, 16. More particularly, a torque of a predetermined amount will release the coupling and cause the bone screw 14, 16 to enter a released mode of operation (FIGS. 5 and 6). In one illustrative embodiment, the predetermined amount of torque is approximately 0.2 Newton-meters. In the secured mode of operation of FIGS. 3 and 4, axial movement of the bone screw 14, 16 is resisted by preventing rotation of the bone screw 14, 16 within the receiving opening 23, 25. In the released mode of operation of FIGS. 5 and 6, the threads 68 and 69 are permitted to rotate relative to one another such that axial movement of the bone screw 14, 16 is permitted.

Tips 58 of the pre-attached screws 14, 16 illustratively protrude a distance 72 beyond the lower surface 70 of the staple 12 towards the target bone 48. In one illustrative embodiment (FIGS. 1 and 2), a cylindrical portion 74 of the protruding distance 72 is a smaller diameter than the minor diameter of the screw threads 68. The screw tips 58 and cylindrical portions 74 and act as awls for piercing cortical bone 48. The preassembled implant device 10 may be mechanically driven into bone. Once the staple legs 18, 20 and screws 14, 16 have pierced the cortical bone 48 a significant distance, usually most of the protruding distance 72, the screws 14, 16 can be tightened to secure the staple 12 to the underlying bone 48. Drill features 76, illustratively cutting edges, assist in clearing bone as the screws 14, 16 are advanced. By piecing the cortical bone 48 prior to tightening the screws 14, 16, the threads 68 have a greater chance of finding purchase in the underlying bone 48 and not jacking the staple 12 back out of the bone 48.

Figure 8:
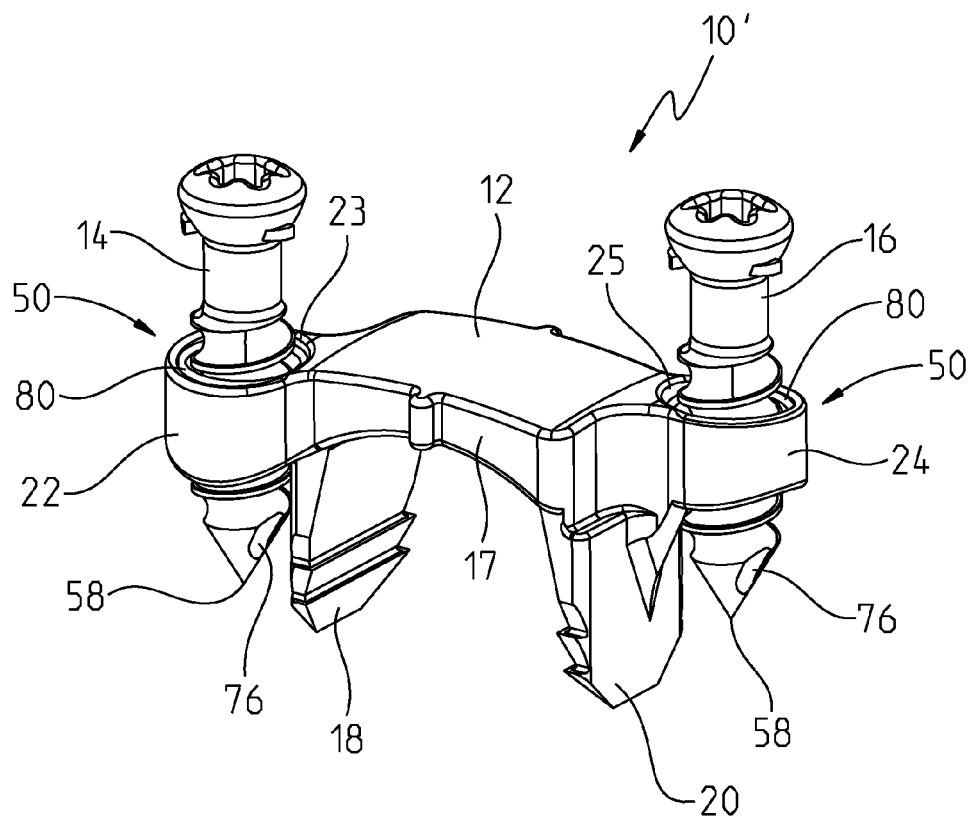
FIG. 8 is an isometric view of a further illustrative orthopedic implant device including pre-attached fasteners.

FIG. 8 shows a further illustrative embodiment implant device 10' wherein the resilient releasable securing member 50 comprises a resistive material 80, positioned intermediate the body 12 and the respective bone screw 14, 16. The resistive material 80 is configured to couple the bone screw 14, 16 to the body and more particularly the male and female threads 68 and 69 of the bone screw 14, 16 and the receiving opening 23, 25 in order to resist rotational and subsequent axial movement of the bone screw 14, 16 relative to the receiving opening 23, 25. Illustratively, the resistive material 80 may comprise a resilient material, such as an elastomeric ring. Alternatively, the resistive material 80 may comprise a wax, an adhesive, or a viscous fluid positioned intermediate the threads 68 and 69 to prevent rotational movement therebetween.

Figure 9:
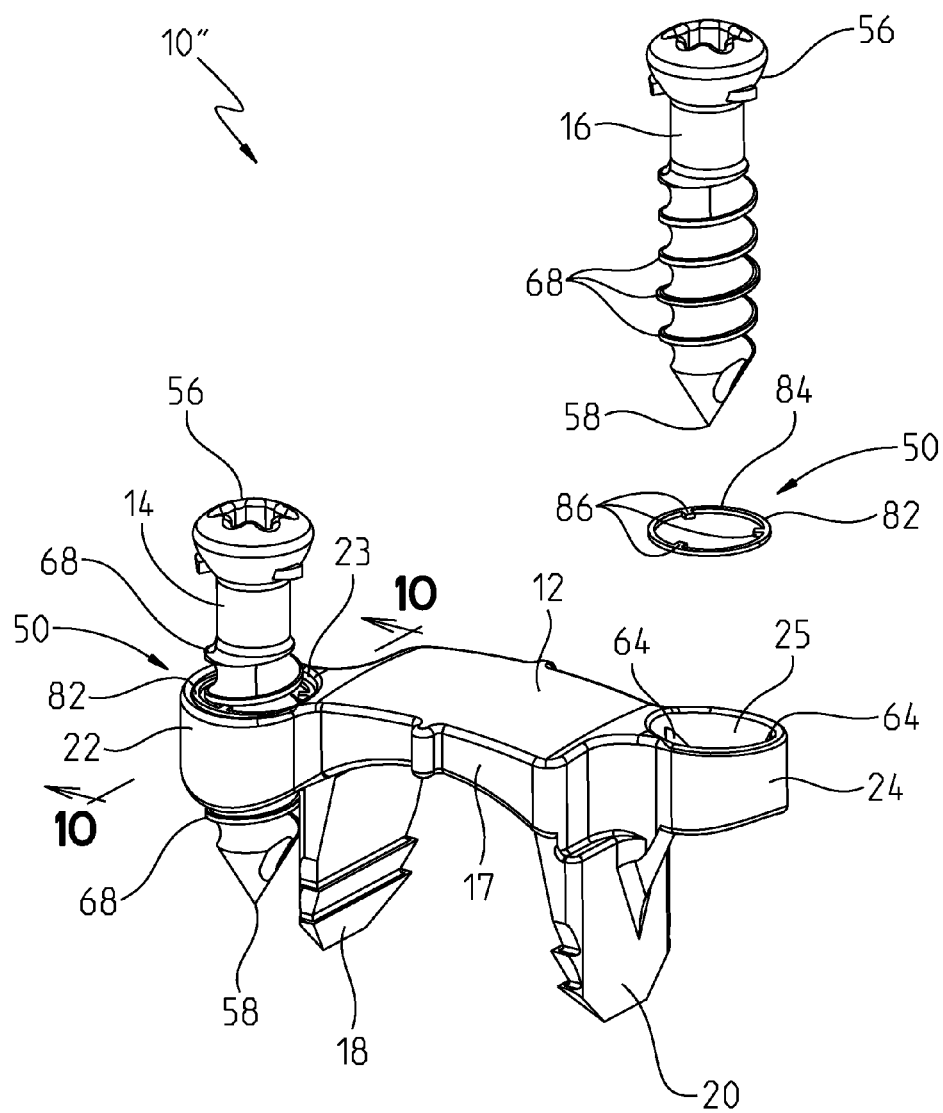
FIG. 9 is a partially exploded isometric view of a further illustrative orthopedic implant device including pre-attached fasteners.
Figure 10:
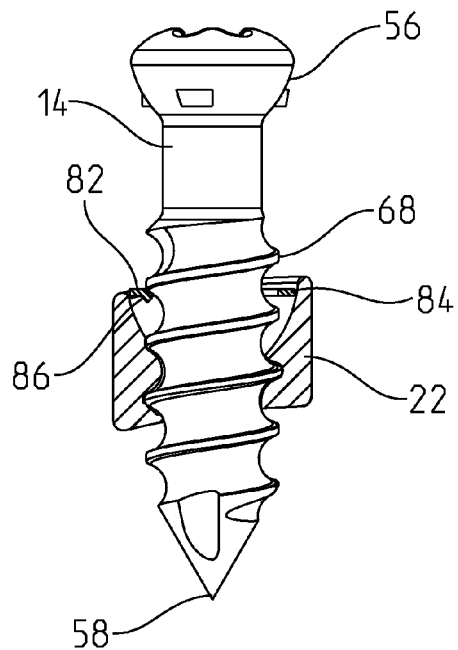
FIG. 10 is a cross-sectional view taken along line 10-10 of FIG. 9 with the bone screw in a secured mode.
Figure 11:
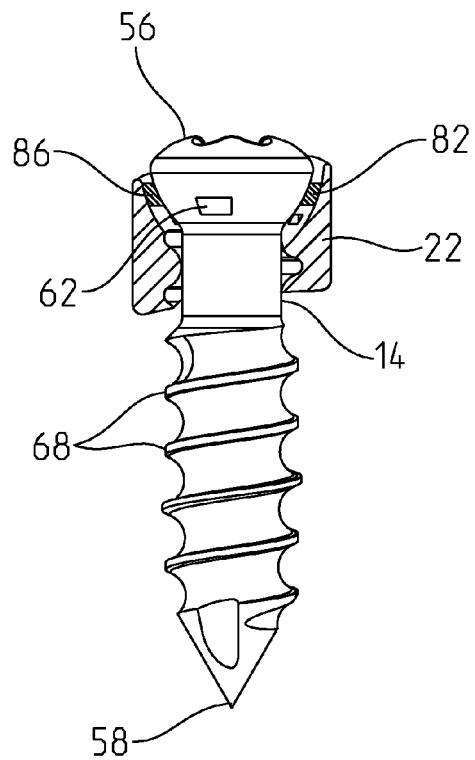
FIG. 11 is a cross-sectional view similar to FIG. 10 showing the bone screw in a locked (down) position.
Figure 15:
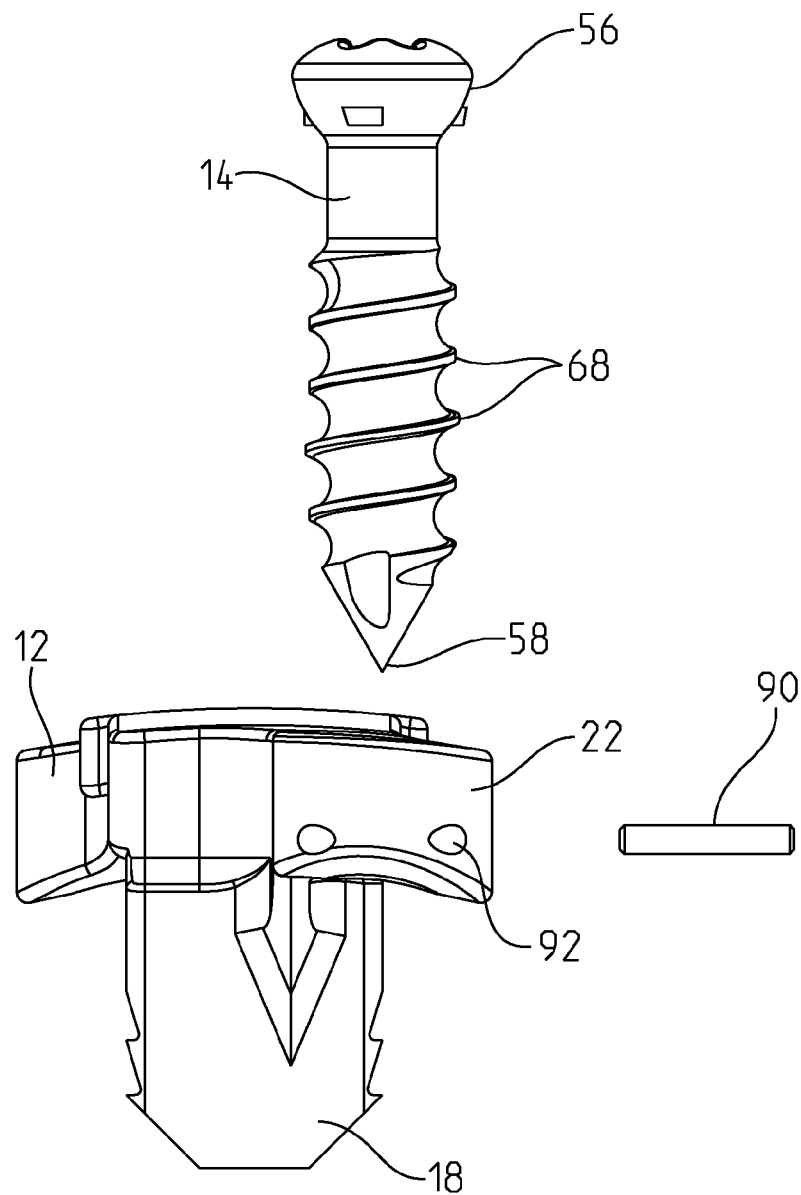
FIG. 15 is an exploded isometric view of a further illustrative orthopedic implant device including pre-attached fasteners.

With reference to FIGS. 9-11, in a further illustrative embodiment implant device 10" the releasable securing member 50 comprises a retaining clip or washer 82. More particularly, the retaining clip 82 is received within each receiving opening 23, 25 and frictionally secured in position relative to the body 12. The retaining clip 82 includes an annular member 84 concentrically received within the fastener receiving opening 23, 25 and including a plurality of radially inwardly extending tabs 86. The tabs 86 are configured to resist movement of the external threads 68 of the bone screw 14, 16 relative to the internal threads 69 of the receiving opening 23, 25 in the secured mode of operation (FIG. 10).

More particularly, the tabs 86 interfere with and push upward on at least one screw thread 68 so that the screw 14, 16 is held in tension between the internal threads 69 and the tabs 86. This tension force prevents movement of the screw 14, 16 due to shock or vibration that could occur during handling and placement of the implant device 10". By applying predetermined torque to the bone screw 14, 16, the tabs 86 are deformed downwardly and as such no longer interfere with rotational movement of the bone screw 14, 16 relative to the internal threads 69 of the receiving opening 23, 25. In other words, when the screw 14, 16 is turned down in the internal threads 69, the tabs 86 are deformed downward to fit between the screw 14, 16 and the clip 82. In the released mode of operation, the bone screw 14, 16 may be rotated relative to the body 12 in order to insert the bone screw 14, 16 into bone 48 until the screw head 56 is locked in a down position with receiving portion 22 (FIG. 11).

With reference now to FIGS. 12-14, in a further illustrative embodiment, the releasable securing member 50 may comprise one or more deformable tabs 88 secured to the body 12 and extending radially inwardly into the receiving openings 23 and 25. In a manner similar to that detailed above with respect to the retaining clip 82 of FIGS. 6-8, each tab 88 interferes with an external thread 68 and is deformable by rotating the respective bone screw 14, 16 from a secured mode of operation (FIG. 13) to a released mode of operation. FIG. 14 shows tab 88 deformed by rotation of screw 14 to a locked (down) position. The tabs 88 may be separate components or may be formed integral with the implant body 12.

With reference now to the further embodiment of FIGS. 15-18, the releasable securing member 50 may comprise a deformable pin 90 inserted within an aperture 92 extending into a respective one of the receiving openings 23, 25. The pin 90 interferes with the screw threads 68 and holds the screw 14, 16 in place. The pin 90 may be formed of a polymer, such as a thermoplastic. The pin 90 is illustratively deformed and moved out of the way by the screw 14, 16 when driven in rotation by applying a predetermined torque.

Figure 19:
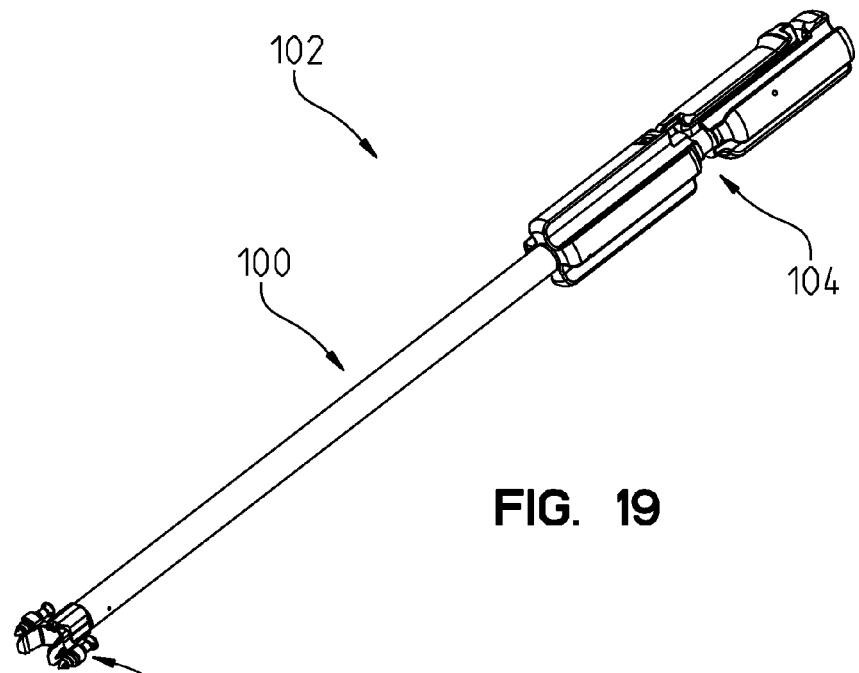
FIG. 19 is an isometric view of the implant body and fasteners of FIG. 1 coupled to an insertion tool.

FIG. 19 shows the implant device 10 held by insertion tool 100 to create a loaded insertion tool 102. Grabbing and releasing device 105 is controlled by the handle 104.

Figure 20:
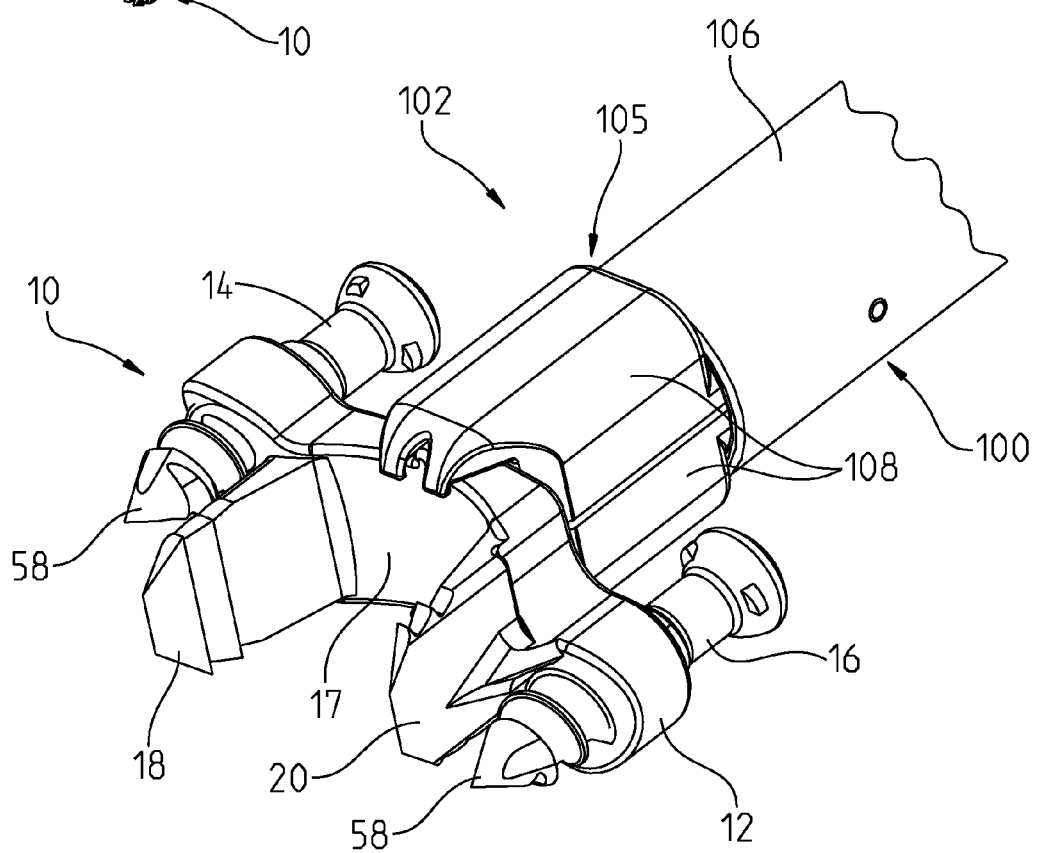
FIG. 20 is an enlarged isometric view of the end effector of the insertion tool of FIG. 19 coupled to the implant body.

FIG. 20 shows the distal portion of loaded insertion tool 100. The distal portion shows the shaft 106 and jaws 108 of insertion tool 100. The jaws 108 hold the staple 12 which in turn holds the screws 14, 16. Staple legs 18, 20 and screw tips 58 are exposed distally.

FIG. 21 shows the position of the screws 14, 16 after tightening in the bone 48 of vertebra 40 with the staple 12 bridging the disc 46. Screws 14, 16 have been advanced into the bone 48 of vertebra 40 to secure the staple 12.

By pre-attaching the screws 14, 16 and having a portion of the screws 14, 16 exposed and unthreaded, cortical bone 48 can be pierced by the screws 14, 16 during staple placement. In relation to existing devices, the illustrative embodiment reduces the number of procedural steps by pre-assembling the implant and fasteners prior to placement.

The illustrative embodiment may also eliminate the need for a separate awl and the steps required to use it into a simpler method for placing the staple. It furthermore eliminates the potential for dropping fasters and the time required to place each screw. The method reduces the number of steps required for surgery therefore minimizing the total surgical procedure time. Reduced time under anesthesia reduces patient risk and operating room costs.

An illustrative method may include the steps of planning and pre-cutting the bone with an osteotome including a needle to establish a datum hole as disclosed in PCT International Application No. PCT/US06/036884, filed Sep. 21, 2006, the disclosure of which is expressly incorporated by reference herein. The method further illustratively includes the following steps:
1. Providing an implant body 12 including fastener receiving openings 23, 25.
2. Inserting fasteners 14, 16, illustratively bone screws, to the implant body 12.
3. Securing the fasteners 14, 16 to the implant body 12 to resist axial movement of the fasteners 14, 16 relative to the receiving opening 23.
4. Using the blunt wire or pin as a datum for locating and placing the implant body 12 (optional).
5. Inserting the implant body 12 in the bone 48 via the insertion tool 100 using mechanical energy (impact force, ultrasonic or sonic energy, reciprocating motion, or other) and simultaneously inserting the fasteners 14, 16.
6. Disengaging the insertion tool 100 to release the implant body 12 and fasteners 14, 16.
7. Applying a predetermined force to the fasteners 14, 16 in order to release the fasteners 14, 16 for axial movement relative to the implant body 12.
8. Inserting the fasteners 14, 16 into bone 48.
9. Tightening the individual fasteners 14, 16.

Although the invention has been described in detail with reference to certain preferred embodiments, variations and modifications exist within the spirit and scope of the invention as described and defined in the following claims.

The invention claimed is:

1. A pre-assembled implant device comprising:
an orthopedic implant including an upper surface and a lower surface; and
a bone screw pre-attached to the implant in a secured mode of operation resisting axial movement of the bone screw relative to the implant prior to placement within a bone, wherein increased torque will cause the bone screw to enter a released mode of operation following the secured mode of operation permitting rotational movement and resulting axial movement of the bone screw in a direction toward the bone, the bone screw extending between proximal and distal ends, including a head supported at the proximal end, and including a bone engaging tip supported at the distal end, wherein the bone engaging tip of the bone screw extends below the lower surface of the orthopedic implant in the secured mode of operation;
wherein the implant includes a spinal staple having a receiving opening with an internal thread, and the bone screw includes an external thread configured to interfere with the internal thread and thereby pre-attach the bone screw to the spinal staple;
wherein at least one revolution of the external thread has a major diameter greater than a minor diameter of the internal thread; and
wherein the head of the bone screw includes a radially outwardly extending protrusion, and the receiving opening of the spinal staple includes a recess, the protrusion and the recess configured to interlock and prevent backout of the bone screw following bone engagement.

2. An orthopedic implant device comprising:
a body having a first surface, a second surface opposed to the first surface and configured to face a bone, and a fastener receiving opening extending between the first and second surfaces;
a bone screw received within the fastener receiving opening of the body and configured to be inserted into the bone, the bone screw extending between proximal and distal ends and including a threaded portion, a head supported at the proximal end, and a bone engaging tip supported at the distal end;

a releasable securing member configured to pre-attach the bone screw to the body prior to placement of the bone screw within the bone in a secured mode of operation resisting axial movement of the bone screw relative to the fastener receiving opening of the body, wherein an applied torque will cause the bone screw to enter a released mode of operation following the secured mode of operation permitting rotational movement and resulting axial movement of the bone screw within the fastener receiving opening of the body in a direction from the first surface toward the second surface, and the bone engaging tip of the bone screw extends beyond the second surface of the body in the secured mode of operation;

wherein the receiving opening of the body includes an internal thread and the threaded portion of the bone screw includes an external thread, the releasable securing member being configured to resist rotational movement and resulting axial movement of the bone screw in the secured mode of operation, and to permit rotational movement and resulting axial movement of the bone screw within the receiving opening in the released mode of operation;

wherein the releasable securing member comprises a single interfering revolution of the external thread providing an interference fit with the internal thread;

wherein the interfering revolution of the external thread has a major diameter greater than a major diameter of the internal thread;

wherein the external thread includes a non-interfering revolution configured to permit rotation relative to the internal thread in the released mode of operation; and wherein the non-interfering revolution of the external thread has a major diameter less than the major diameter of the interfering revolution of the external thread and sized to rotate relative to the internal thread in the released mode of operation.

3. The orthopedic implant device of claim 2, wherein a torque of at least about 0.2 Newton-meters is required to release the securing member.

4. The orthopedic implant device of claim 2, wherein the releasable securing member comprises a deformable member supported by the body and extending within the receiving opening.

5. The orthopedic implant device of claim 2, wherein the head of the bone screw includes a protrusion, and the receiving opening of the body includes a recess, the protrusion and the recess configured to interlock and prevent back-out of the bone screw following bone engagement.

6. The orthopedic implant device of claim 2, wherein the body comprises a spinal staple having a bridge member, a pair of legs coupled to opposing ends of the bridge member, and a pair of fastener retaining portions defining a pair of the fastener receiving openings.

7. An orthopedic implant device comprising:

a spinal staple including a bridge member having an upper surface, an opposed lower surface, a first end, an opposed second end, a first leg proximate the first end and configured to be inserted into a first vertebra, a second leg proximate the second end and configured to be inserted into a second vertebra, a fastener retaining portion extending from the bridge member first end and including an upper surface, a lower surface and a fastener receiving opening extending between the upper surface of the fastener retaining portion and the lower surface of the fastener retaining portion, the lower surface of the fastener retaining portion configured to face the first vertebra;

a fastener configured to couple the spinal staple to the first vertebra, and including a bone engaging tip configured to penetrate the first vertebra;

a releasable securing member configured to pre-attach the fastener to the spinal staple in a secured mode of operation resisting axial movement of the fastener relative to the spinal staple prior to coupling of the spinal staple to the first vertebra and the second vertebra, wherein an applied torque will cause the fastener to enter a released mode of operation following the secured mode of operation permitting rotational movement and resulting axial movement of the fastener in a direction toward the first vertebra, the fastener extending from the lower surface of the fastener retaining portion in the secured mode of operation;

wherein the fastener comprises a bone screw received within the fastener receiving opening of the spinal staple and configured to be inserted into the first vertebra, the bone screw including an elongated shank extending between proximal and distal ends and including a threaded portion, the releasable securing member configured to resist axial movement of the bone screw relative to the fastener receiving opening of the spinal staple in the secured mode of operation;

wherein the fastener receiving opening of the spinal staple includes at least one internal thread and the threaded portion of the bone screw includes at least one external thread, and the releasable securing member comprises an interfering revolution of the external thread providing an interference fit with the internal thread;

wherein the interfering revolution of the external thread has a major diameter greater than a major diameter of the internal thread;

wherein the external thread includes a non-interfering revolution configured to permit rotation relative to the internal thread in the released mode of operation; and wherein the non-interfering revolution of the external thread has a major diameter less than the major diameter of the interfering revolution of the external thread and sized to rotate relative to the internal thread in the released mode of operation.

8. The orthopedic implant device of claim 7, wherein a torque of at least about 0.2 Newton-meters is required to release the securing member.

9. The orthopedic implant device of claim 7, wherein the releasable securing member comprises a deformable member supported by the spinal staple and extending within the receiving opening.

10. The orthopedic implant device of claim 7, wherein the bone screw includes a head having at least one protrusion, and the receiving opening of the spinal staple includes at least one recess, the protrusion and the recess configured to interlock and prevent back-out of the bone screw following bone engagement.

* * * * *